US012303382B2

United States Patent
Malave-Robles et al.

(10) Patent No.: US 12,303,382 B2
(45) Date of Patent: May 20, 2025

(54) INTRAOCULAR LENS LOAD ASSEMBLY SYSTEM

(71) Applicant: Johnson & Johnson Surgical Vision, Inc., Irvine, CA (US)

(72) Inventors: Usiel Malave-Robles, Anasco, PR (US); John Scott, Limerick (IE)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 82 days.

(21) Appl. No.: 18/464,180

(22) Filed: Sep. 8, 2023

(65) Prior Publication Data
US 2024/0081978 A1 Mar. 14, 2024

Related U.S. Application Data

(60) Provisional application No. 63/375,513, filed on Sep. 13, 2022.

(51) Int. Cl.
| | | |
|---|---|---|
| *B25J 11/00* | (2006.01) | |
| *A61F 2/16* | (2006.01) | |
| *B25J 9/16* | (2006.01) | |
| *B65B 23/00* | (2006.01) | |
| *B65B 25/00* | (2006.01) | |

(52) U.S. Cl.
CPC ........... *A61F 2/1691* (2013.01); *B25J 9/1697* (2013.01); *B65B 23/00* (2013.01)

(58) Field of Classification Search
CPC ..... B25J 9/1697; B25J 11/0095; B65B 23/00; B65B 25/008; B65B 25/00
See application file for complete search history.

(56) References Cited

U.S. PATENT DOCUMENTS

| | | | | | |
|---|---|---|---|---|---|
| 5,186,599 | A | * | 2/1993 | Fluck | ............... B65G 43/08 414/792.9 |
| 5,195,234 | A | * | 3/1993 | Pine | ............... H05K 13/0812 29/739 |
| 5,256,029 | A | * | 10/1993 | Fluck | ............... B65B 23/14 414/792.9 |
| 5,528,878 | A | * | 6/1996 | Edwards | ............ G05B 19/4189 53/54 |
| 5,561,970 | A | * | 10/1996 | Edie | ............... B65B 57/10 53/251 |

(Continued)

FOREIGN PATENT DOCUMENTS

| | | |
|---|---|---|
| EP | 2301478 A1 | 3/2011 |
| WO | 2023021374 A1 | 2/2023 |

*Primary Examiner* — Gloria R Weeks

(57) ABSTRACT

A method for providing automatic placement of a lens in a cartridge is provided. The method includes seizing, by a nozzle head of a lifting tool, the lens from a pick position of a platform based on an air flow through the nozzle head and depositing, by the lifting tool, the lens at a delivery point in the cartridge by changing the air flow through the nozzle head. The method includes determining, by a processor coupled to the lifting tool, a location of a haptic of the lens with respect to a feature of the cartridge. The method includes adjusting, by the lifting tool, the haptic from the location to a target orientation on the cartridge when the location of the haptic is determined to be misaligned with the feature. The method can be implemented as an apparatus, a system, and/or a computer program product.

20 Claims, 8 Drawing Sheets

(56) References Cited

U.S. PATENT DOCUMENTS

| | | | | |
|---|---|---|---|---|
| 5,578,331 | A * | 11/1996 | Martin | B29D 11/0024 |
| | | | | 264/2.6 |
| 5,623,816 | A * | 4/1997 | Edwards | B29C 66/849 |
| | | | | 53/499 |
| 5,706,634 | A * | 1/1998 | Edwards | B65B 55/22 |
| | | | | 53/247 |
| 6,502,876 | B1 * | 1/2003 | Stockhorst | B29D 11/0024 |
| | | | | 294/183 |
| 6,558,584 | B1 * | 5/2003 | O'Neill | B29D 11/00192 |
| | | | | 264/2.6 |
| 6,701,694 | B2 * | 3/2004 | Huppi | B25J 11/0045 |
| | | | | 53/251 |
| 7,637,084 | B2 * | 12/2009 | Aikenhead | B65D 31/16 |
| | | | | 53/445 |
| 8,065,035 | B2 * | 11/2011 | Ross | G16H 20/13 |
| | | | | 53/411 |
| 12,176,234 | B2 * | 12/2024 | Jung | B25J 11/0095 |
| 2002/0095909 | A1 * | 7/2002 | Duncan | B29C 66/131 |
| | | | | 53/329.2 |
| 2005/0045589 | A1 * | 3/2005 | Rastogi | B29C 59/14 |
| | | | | 427/569 |
| 2013/0103179 | A1 * | 4/2013 | Miyoshi | B25J 9/1697 |
| | | | | 700/228 |
| 2014/0331602 | A1 * | 11/2014 | Newman | B29C 66/8432 |
| | | | | 53/422 |
| 2014/0348622 | A1 * | 11/2014 | Yamazoe | H01L 21/67259 |
| | | | | 414/744.2 |
| 2015/0232219 | A1 * | 8/2015 | Kern | B65B 5/106 |
| | | | | 53/443 |
| 2019/0125524 | A1 * | 5/2019 | Huehn | A61F 9/0061 |
| 2021/0252694 | A1 * | 8/2021 | Toyomaki | H01L 21/67766 |
| 2023/0048115 | A1 * | 2/2023 | Kim | B65G 47/91 |

* cited by examiner

METHOD 200

```
┌─────────────────────────────────────────────────────────────┐
│  Seizing, by a nozzle head of a lifting tool, the lens from a pick │
│  position of a platform based on an inward air flow through the nozzle │
│                           head                              │
│                           210                               │
└─────────────────────────────────────────────────────────────┘
                              │
                              ▼
┌─────────────────────────────────────────────────────────────┐
│  Depositing, by the lifting tool, the lens at a delivery point in the │
│  cartridge by changing the inward air flow through the nozzle head │
│                           230                               │
└─────────────────────────────────────────────────────────────┘
                              │
                              ▼
┌─────────────────────────────────────────────────────────────┐
│  Determining, by at least one processor coupled to the lifting tool, a │
│  location of a haptic of the lens with respect to a feature of the │
│                         cartridge                           │
│                           250                               │
└─────────────────────────────────────────────────────────────┘
                              │
                              ▼
┌─────────────────────────────────────────────────────────────┐
│  Adjusting, by the lifting tool, the haptic from the location to a target │
│  orientation on the feature of the cartridge when the location of the │
│       haptic is determined to be misaligned with the feature │
│                           270                               │
└─────────────────────────────────────────────────────────────┘
```

FIG. 2

INTRAOCULAR LENS LOAD ASSEMBLY SYSTEM

CROSS-REFERENCE TO RELATED PATENT APPLICATIONS

This application claims priority to U.S. Provisional Application No. 63/375,513, filed on Sep. 13, 2022, which is hereby incorporated by reference in its entirety.

FIELD OF INVENTION

This disclosure is related to automated systems and methods for loading an intraocular lens (IOL) into a cartridge. More particularly, a load assembly system utilizes vacuum and gripper technologies to provide automatic placement of an IOL into a cartridge.

BACKGROUND

Generally, in ophthalmology, a surgeon who is implanting an IOL as part of a surgical procedure requires the IOL to be placed into a cartridge portion of an insertion system prior to insertion. This cartridge is typically designed to hold the lens and facilitate its folding as the lens is advanced through the insertion system into the eye.

There are two broad categories of insertion systems. In conventional IOL packaging, a nurse or assistant in the surgical suite manually loads an IOL into a cartridge prior to surgery. More recently, preloaded systems have become available where the lens is provided in a preloaded configuration so there is no requirement for manual loading in the surgical suite. However, such preloaded systems are still manually loaded as part of the manufacturing process. While people can be trained on appropriate loading techniques, it is a process that should not be rushed. There is also the possibility of human error during the transfer. An automated system that is configured to load an IOL into a cartridge could remove the human error and provide speed in manufacturing.

SUMMARY

According to an embodiment, a method is provided. The method provides automatic placement of a lens in a cartridge. The method includes seizing, by a nozzle head of a lifting tool, the lens from a pick position of a platform based on an air flow through the nozzle head and depositing, by the lifting tool, the lens at a delivery point in the cartridge by changing the air flow through the nozzle head. The method includes determining, by at least one processor coupled to the lifting tool, a location of a haptic of the lens with respect to a feature of the cartridge and adjusting, by the lifting tool, the haptic from the location to a target orientation on the cartridge when the location of the haptic is determined to be misaligned with the feature. According to one or more embodiments, the method embodiment above can be implemented as an apparatus, a system, and/or a computer program product.

According to an embodiment, a system is provided. The system provides automatic placement of a lens in a cartridge. The system includes a lifting tool that includes a nozzle head. The lifting tool is configured to seize the lens from a pick position of a platform based on an air flow through the nozzle head, deposit the lens at a delivery point in the cartridge by changing the air flow through the nozzle head, and adjust a haptic of the lens from a location of the haptic to a target orientation on the cartridge when the location of the haptic is determined to be misaligned with a feature of the cartridge. The system includes at least one processor coupled to the lifting tool. The at least one processor is configured to determine the location of the haptic with respect to the feature of the cartridge. According to one or more embodiments, the system embodiment above can be implemented as an apparatus, a method, and/or a computer program product.

BRIEF DESCRIPTION OF THE DRAWINGS

A more detailed understanding may be had from the following description, given by way of example in conjunction with the accompanying drawings, wherein like reference numerals in the figures indicate like elements, and wherein:

FIG. 2 illustrates a method according to one or more embodiments;

DETAILED DESCRIPTION

Generally, disclosed herein are systems and methods for IOL packaging. More particularly, systems and methods herein provide loading the IOL into a cartridge, by way of a load assembly system that utilizes vacuum and gripper technologies to provide automatic placement of the IOL into the cartridge.

Figure 1:
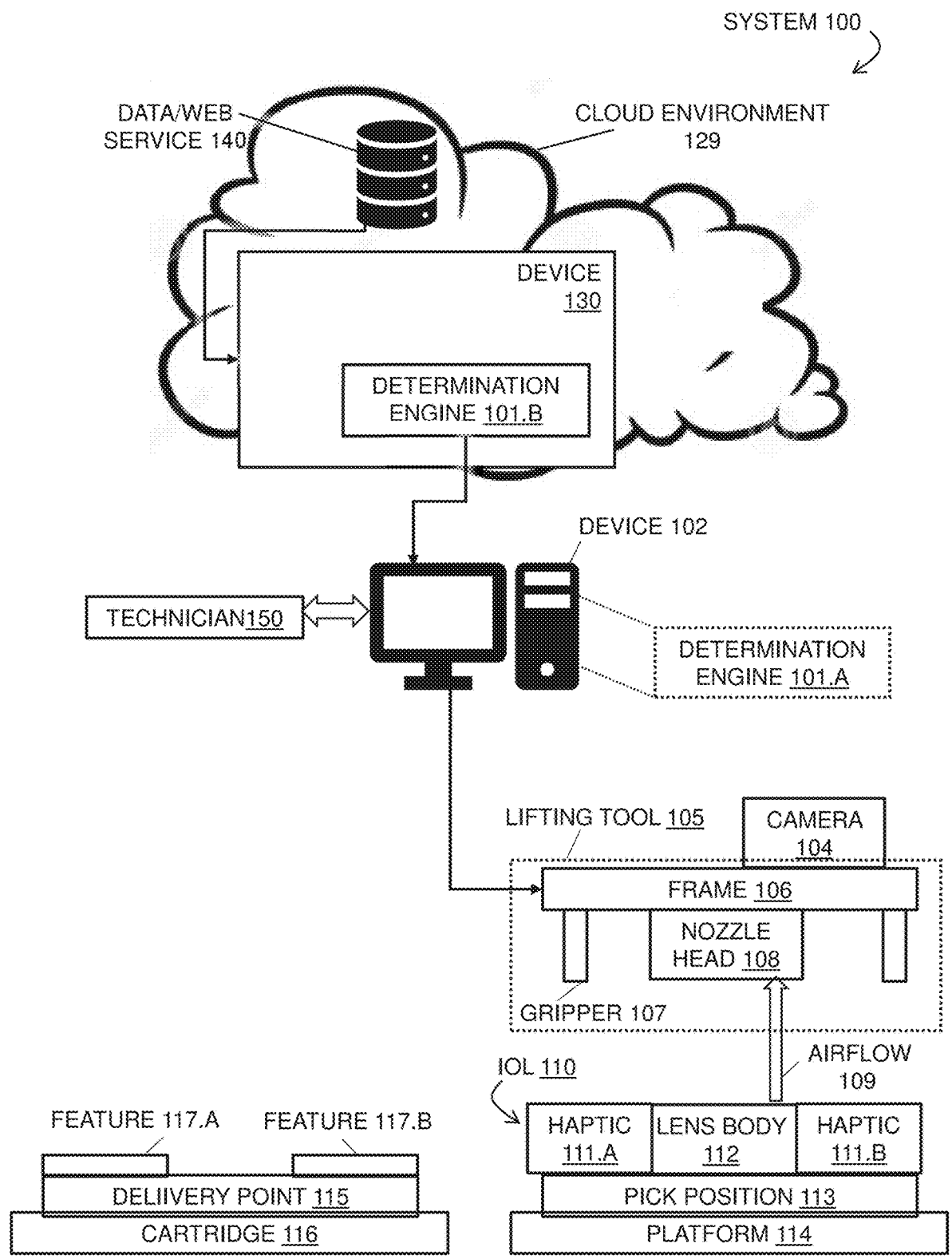
FIG. 1 illustrates a system according to one or more embodiments.

FIG. 1 illustrates a system 100 (e.g., a load assembly system) according to one or more embodiments. The system 100 can generally be viewed as a combination of assembly, sensor, process, diagnostic, and user equipment. Note that items and elements of the system 100, while shown in the singular, are representative of one or more of that item or element. To implement automatic placement, the system 100 implements one or more instances of a determination engine 101. According to one or more embodiments, the determination engine 101 can be configured in hardware, software, or a hybrid implementation. For example, determination engine 101 can be stored as software components, modules, engines, instructions, or the like for execution by a processor (as described herein) to cause the system 100 to operate. Note that the determination engine 101 can be viewed as a combination of instructions/software across the system 100, including client instances (e.g., the determination engine 101.A) that communicates with other elements of the system 100 (e.g., the determination engine 101.B can be a server instance). For example, the determination engine 101 can have a specific software instances that implement particular operations of the system 100 itself. The system also includes a device 102 (e.g., that includes at least one processor and a memory) and a camera 104, as further described herein.

The system 100 includes a lifting tool 105. The lifting tool 105 can include a frame 106, one or more grippers 107, and a nozzle head 108, as well as any motors, compressors, airways, gears, bearings, lubricants, sensors, circuits, wiring, lighting, and the like to result in seizing, moving, and depositing of the IOL 110 based on communications to/from the determination engine 101. The frame 106 includes one or more members, each of which can articulate and move with respect to x-y-z directions and each other, such as by electrical motors. The one or more members can be made of any material, such as metal, plastic, rubber, wood, etc. Each of the one or more grippers 107 can be a bar or rod member extending from the frame 106. Each of the one or more grippers 107 can be movable with respect to z-y-z directions, such as by electrical motors.

The nozzle head 108 can provide airflow 109 on a IOL 110. The IOL 110 is an artificial implant that is used to replace a natural crystalline lens in an eye, as part of a treatment for cataracts or myopia (e.g., typically implanted during cataract surgery, after the eye's cloudy natural lens has been removed). The IOL 110 can includes a lens body 112 and one or more haptics 111. The lens body 112 (e.g., a small plastic lens) provides a same light-focusing function as the natural crystalline lens. The one or more haptics 111 (e.g., plastic side struts) hold the IOL 110 in place in a capsular bag inside the eye.

The airflow 109 can be along an inward direction to create a direct suction on the IOL 110 or along an outward direction to create a suction effect according to the Bernoulli principle. According to one or more embodiments, the nozzle head 108 contacts an outer periphery of the lens body 111 of the IOL 110 while the airflow 109 is enables. By way of example, the nozzle head 108 can be configured to leverage the Bernoulli principle to provide a suction effect used to lift the IOL 110, while applying limited pressure thereto. The lifting tool 105, based on the configuration of the nozzle head 108 and use of the Bernoulli principal, contacts only non-optical portions of the IOL 110 (e.g., minimally contacts the outer periphery of the lens body 111) during the seizing of the IOL 110.

According to one or more embodiments, the one or more grippers 107 can be associated in pairs and match or correspond to the haptics 111 of the IOL 110. The one or more grippers 107, generally, do not engage or contact the IOL 110 at the picking/seizing/depositing moments of the automatic placement operations. The one or more grippers 107, rather, engage the IOL 110 post placement/deposition to enable a smart-load operations. In this regard, for example, a pair of first grippers 107 can adjust the haptic 111.A with respect to the first feature 117.A. Then, a pair of second grippers 107 can adjust the haptic 111.B with respect to the second feature 117.B. Examples of the one or more grippers 107 include, but are not limited to, electric grippers, piezoelectric actuator-based grippers, large-displacement microgripper, haptic gripper, and robot gripper. As used herein, the terms feature is used to refer to a location in a cartridge that is designed for haptic placement. By way of example, and not of limitation, the feature may be a seat, a ledge, a ramp, a detent, a protrusion, a gap or any other feature that a haptic may be place on, adjacent to, abutting, or under.

The IOL 110 can be initially positioned at a pick position 113 of a platform 114. The lifting tool 110 can secure and move the IOL 110 from the pick position 113 to a delivery point 115 of a cartridge 116 (e.g., a lens module), such as on one or more features 117. The pick position 113 of the platform 114 can correspond to how the IOL 110 is being delivered post manufacturing (e.g., via an manufacturing line or within a transport container). The delivery point 115 of the cartridge 116 can correspond to a packaging of the IOL 110 (e.g., at a cartridge line). Note that the IOL 110 is loaded into the cartridge 116 so that the IOL 110 can be properly folded without being damaged. Once folded and during surgery, the IOL 110 can be provided into an eye through a small incision (e.g., less than an unfolded size of the IOL 110) and unfolder while in the eye. It is imperative that the IOL 110 is properly placed in the cartridge 116, and on the one or more features 117, so that the IOL 110 remains undamaged throughout the surgery.

The system 100 also includes a cloud environment 129. The cloud environment 129 may be a wired network, a wireless network, and/or include one or more wired and wireless networks, such as an intranet, a local area network (LAN), a wide area network (WAN), a metropolitan area network (MAN), a short-range network, a direct connection or series of connections, a cellular telephone network, or any other network or medium capable of facilitating communication between the items of FIG. 1 using any one of various communication standards/protocols (e.g., Bluetooth, Wi-Fi, Zigbee, Z-Wave, near field communications (NFC), Zigbee, infrared (IR), Ethernet, Universal Serial Bus (USB), or any other communication standards/protocols). Additionally, several networks may work alone or in communication with each other to facilitate communication in the cloud environment 129.

The cloud environment 129 includes a device 130 (e.g., a remote computing system) and a data/web service 140, each of which can includes at least one processor and a memory as further described herein. In some instances, the device 130 and/or the data/web service 140 may be implemented as a single physical server on the cloud environment 129. In other instances, the device 130 and/or the data/web service 140 may be implemented as a virtual server a public cloud computing provider of the cloud environment 129. The data/web service 140 can database (e.g., an SQL database) and/or another storage mechanism. Thus, the data/web service 125 can be used as a repository for storage across the system 100. According to one or more embodiments, the data/web service 140 can store data, as well as machine learning (ML) models, determination models, driver components, native APIs, and the like for use by the determination engine 101. According to one or more embodiments, the data is any form of quantities, statistics, measurements, visual information, device speed, airflow information, dates, identifiers, and the like from any source, as well as predictors associated therewith. By way of example, the device 102 can generate measurements from the visual information of the one or more images. The measurements can include, but is not limited to, haptic locations, distances between the haptic 111 and a wall of a feature 117.

Any of the memories of the device 102, the device 130, and the data/web service 140 can include an instance of the determination engine 101 (e.g., the determination engine 101.A resides on the device 102, and the determination engine 101.B resides on the device 130). Generally, the determination engine 101 is executed by at least one processor within the system 100, whether automatically or as directed by a technician 150, to implement an automatic placement operation. According to one or more embodiments, the determination engine 101 can be fully autonomous, as driven by the machine learning and/or an artificial intelligence (ML/AI) and programming described herein. The technician 150 can be any person or persons providing medical treatment and/or care. Example of the technician 150 include, but are not limited to engineers, programmers, assembly workers, factory workers, surgeons, doctors, clinicians, medical staff, nurses, and medical assistants.

Turning to FIG. 2, a method 200 is illustrated according to one or more embodiments. For brevity, like reference numerals in the figures indicate like elements, and objects, elements, items, and reference numerals that are similar to those of previous figures are reused for FIG. 2.

The method 200 depicts an automatic placement operation of the IOL 110 in the cartridge 116 of the system 100. Generally, the automatic placement operation includes when the IOL 110 is provided at the delivery point 115 from the pick position 113 by the nozzle head 108 of the lifting tool 105. The method 200 can be implemented by the determination engine 101.

The method 200 begins at block 210, when the nozzle head 108 of the lifting tool 105 seizes the IOL 110 from the pick position 113 of the platform 114 based on the airflow 109 through the nozzle head 108. At block 230, the lifting tool 105 deposits the IOL 110 at the delivery point 115 in the cartridge 116 by changing (e.g., stopping or reducing) the airflow 109 through the nozzle head 108. Note, according to one or more embodiments, the cartridge 116 can be 'open', such that the IOL 110 is delivered therein (e.g., a lid of a lens module can be in an open position and the delivery point 115, as well as the features 117, are exposed and viewable).

At block 250, the at least one processor (e.g., of the device 102 that is communicatively and operatively coupled to the lifting tool 105) determines a location of at least one of the one or more haptics 111 of the IOL 110 with respect to a matching one of the one or more features 117 of the cartridge 116 (e.g., a first haptic 111.A is determined with respect to a first feature 117.A). At block 270, the lifting tool 105 adjusts the at least one of the one or more haptics 111 from the location to a target orientation on/in the cartridge 116 or on the matching one of the one or more features 117 of the cartridge 116 when there is a misalignments (e.g., the location of the first haptic 111.A is determined to be misaligned with the first feature 117.A). Note, according to one or more embodiments, the cartridge 116 can be 'closed', such that the IOL 110 is contained therein (e.g., a lid of a lens module can be automatically moved into a closed position by a rotating apparatus).

Returning to FIG. 1, the devices 102 and 130 and the data/web service 140 can structurally be any computing device comprising software and/or hardware, such as a general-purpose computer, with suitable interface circuits for transmitting and receiving signals to and from other items of the system 100. By way of example, the devices 102 and 130 and the data/web service 140 can be singular computing devices. By way of example, the device 130 and the data/web service 140 are shown as virtual and/or distributed devices in the cloud environment 129.

Figure 3:
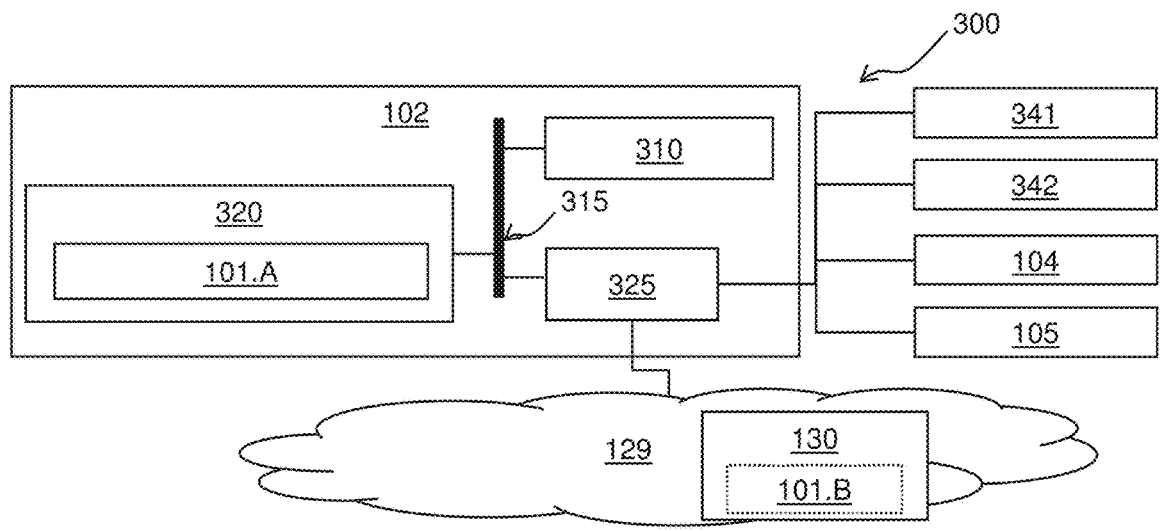
FIG. 3 illustrates a system according to one or more embodiments.

As a representative example of the system 100, FIG. 3 illustrates a system 300 according to one or more embodiments. For brevity, like reference numerals in the figures indicate like elements, and objects, elements, items, and reference numerals that are similar to those of previous figures are reused for FIG. 3.

The system 300 can be representative of any computing apparatus and/or computing environment, which comprise hardware, software, or a combination thereof. Further, embodiments of the system 300 disclosed may include apparatuses, systems, methods, and/or computer program products at any possible technical detail level of integration.

The system 300 shows the device 102 with one or more central processing units (CPU(s)), which are collectively or generically referred to as a processor 310. The processor 310, also referred to as processing circuits, is coupled via a system bus 315 to a system memory 320 and various other components. The device 102 (as well as the device 130 and the data/web service 140) may be adapted or configured to perform as an online platform, a server, an embedded computing system, a personal computer, a console, a personal digital assistant (PDA), a cell phone, a tablet computing device, a quantum computing device, cloud computing device, a mobile device, a smartphone, a fixed mobile device, a smart display, a wearable computer, or the like.

The processor 310 may be any type of general or specific purpose processor, including a central processing unit (CPU), application specific integrated circuit (ASIC), field programmable gate array (FPGA), graphics processing unit (GPU), controller, multi-core processing unit, three dimensional processor, quantum computing device, or any combination thereof. The processor 310 may also have multiple processing cores, and at least some of the cores may be configured to perform specific functions. Multi-parallel processing may also be configured. In addition, at least the processor 310 may be a neuromorphic circuit that includes processing elements that mimic biological neurons. The processor 131, in executing the determination engine 101, may be configured to receive, process, and manage the information of the data/web service 140. The processor 131 can also be representative of cloud processing across the system 100.

The system bus 315 (or other communication mechanism) is configured for communicating signals (and data) to/from the processor 310, the system memory 320, and various other components, such as the adapter 325. The system memory 320 is an example of a (non-transitory) computer readable storage medium, where the determination engine 101 can be stored as software components, modules, engines, instructions, or the like for execution by the processor 310 to cause the device 102 to operate, such as described herein with reference to the figures. The system memory 320 can include any combination of a read only memory (ROM), a random access memory (RAM), internal or external Flash memory, embedded static-RAM (SRAM), solid-state memory, cache, static storage such as a magnetic or optical disk, or any other types of volatile or non-volatile memory. Non-transitory computer readable storage mediums may be any media that can be accessed by the processor 310 and may include volatile media, non-volatile media, or the like. For example, the ROM is coupled to the system bus 315 and may include a basic input/output system (BIOS), which controls certain basic functions of the device 102, and the RAM is read-write memory coupled to the system bus 315 for use by the processors 310. Non-transitory computer readable storage mediums can include any media that is removable, non-removable, or the like. The memory 132 can also be virtualized and distributed across the cloud environment 115.

According to one or more embodiments, the determination engine 101 can be configured in hardware, software, or a hybrid implementation. The determination engine 101 can be composed of modules that are in operative communication with one another, and to pass information or instructions. According to one or more embodiments, the determination engine 101 can provide one or more UIs, such as on behalf of an operating system or other application and/or directly as needed. The UIs include, but are not limited to, graphic UIs (GUIs), window interfaces, internet browsers, and/or other visual interfaces for applications, operating systems, file folders, and the like. Thus, user activity can include any interaction or manipulation of the UIs provided by the determination engine 101. The determination engine 101 can further include custom modules to perform application specific processes or derivatives thereof, such that the computing system 200 may include additional functionality.

Figure 6:
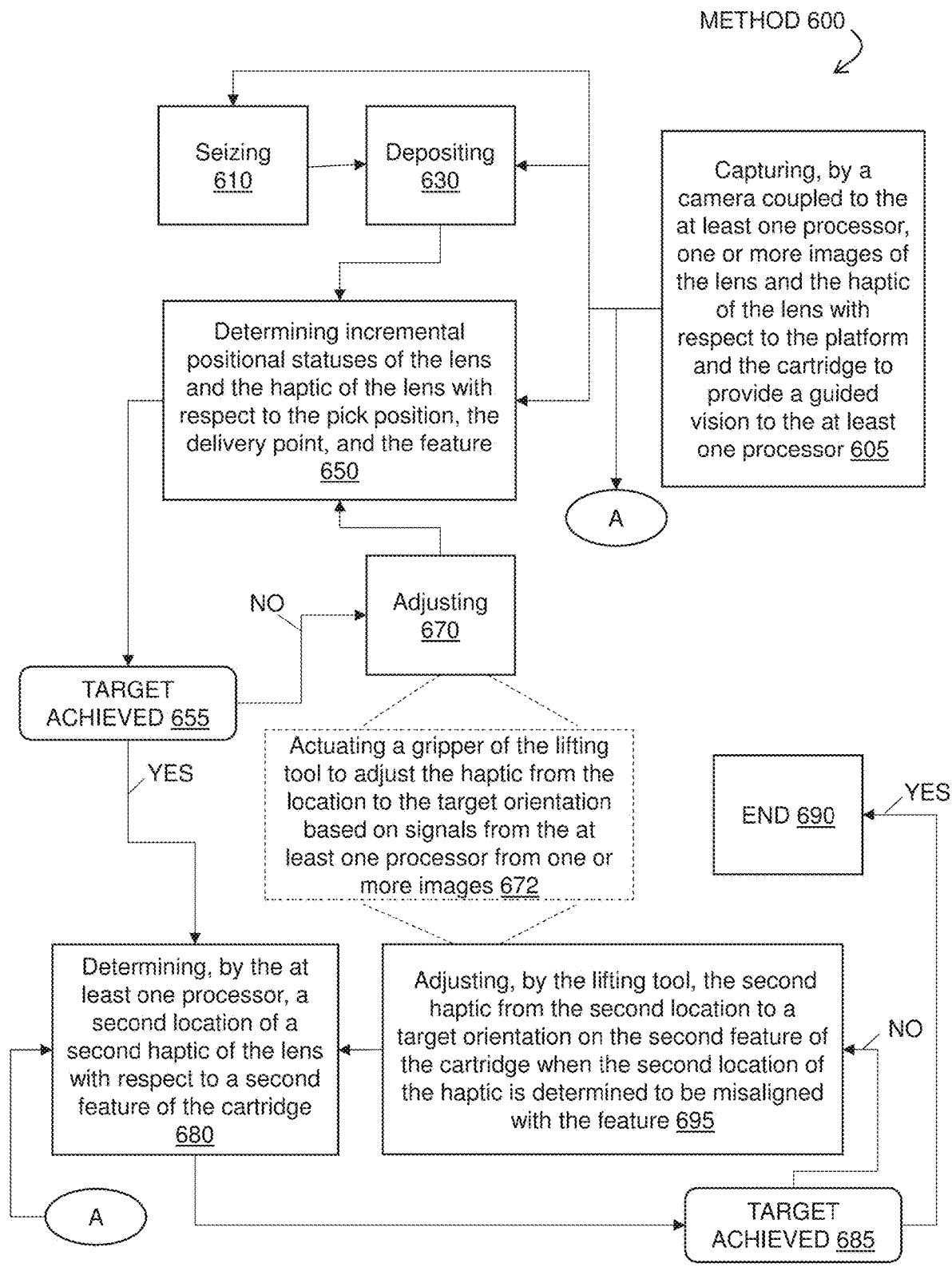
FIG. 6 illustrates a method according to one or more embodiments.

For example, according to one or more embodiments, the determination engine 101 may be configured to store information, instructions, commands, or data to be executed or processed by the processor 310 to logically implement the method 200 of FIG. 2 (as represented by block 210, 230, 250, and 270 within the determination engine 101), as well as a method 600 of FIG. 6. For instance, the determination engine 101 is communicatively and operatively coupled to the lifting tool 105 to send commands thereto and cause operations thereof. The determination engines 101 of FIGS. 1 and 3 can also be representative of an operating system, a mobile application, a client application instance, a server application instance, and/or the like. According to one or more embodiments, the functionality of the device 102 with respect to the determination engine 101 can also be implemented on the device 130 and the data/web service, as represented by separate instances of the determination engine 101.

Further, modules of the determination engine 101 can be implemented as a hardware circuit comprising custom very large scale integration (VLSI) circuits or gate arrays, off-the-shelf semiconductors such as logic chips, transistors, or other discrete components, in programmable hardware devices (e.g., field programmable gate arrays, programmable array logic, programmable logic devices), graphics processing units, or the like. Modules of the determination engine 101 can be at least partially implemented in software for execution by various types of processors. According to one or more embodiments, an identified unit of executable code may include one or more physical or logical blocks of computer instructions that may, for instance, be organized as an object, procedure, routine, subroutine, or function. Executables of an identified module co-located or stored in different locations such that, when joined logically together, comprise the module. A module of executable code may be a single instruction, one or more data structures, one or more data sets, a plurality of instructions, or the like distributed over several different code segments, among different programs, across several memory devices, or the like. Operational or functional data may be identified and illustrated herein within modules of the determination engine 101, and may be embodied in a suitable form and organized within any suitable type of data structure.

Furthermore, modules of the determination engine 101 can also include, but are not limited to, location modules, augmented reality modules, and ML/AI algorithm modules. A location module can be configured can be configured to create, build, store, and provide algorithms and models that determine a location of the lifting tool 105 and relative distances between the haptics 111 and the features 117.

According to more or more embodiments, the location module can implement location, spatial navigation, surveying, distance, direction, and/or time software. An augmented reality module can be configured to create, build, store, and provide algorithms and models that provide interactive experiences with the automatic placement operations of the system 100 where objects (e.g., the haptics 111 and the features 117) that reside in the real world are enhanced by computer-generated perceptual information, sometimes across multiple sensory modalities. A ML/AI algorithm module can be configured to create, build, store, and provide algorithms and models that improve automatically through experience, as well as emulate 'natural' cognitive abilities of humans. In an example, ML software uses training data to build a particular model and to improve that model, while AI software perceives an environment (e.g., receives active data) and takes actions (e.g., applies a model) to solve a problem and/or produce an output. AI software can use a model built by humans and/or ML software. AI software can further provide feedback to the ML software to improve any models thereof. ML/AI can exist independently and/or coexist.

The adapter 325 can be representative of an input/output (I/O) adapter, a communications adapter, and a device adapter.

According to one or more embodiments, the I/O adapter can be configured as a small computer system interface (SCSI), of in view of frequency division multiple access (FDMA) single carrier FDMA (SC-FDMA), time division multiple access (TDMA), code division multiple access (CDMA), orthogonal frequency-division multiplexing (OFDM), orthogonal frequency-division multiple access (OFDMA), global system for mobile (GSM) communications, general packet radio service (GPRS), universal mobile telecommunications system (UMTS), cdma2000, wideband CDMA (W-CDMA), high-speed downlink packet access (HSDPA), high-speed uplink packet access (HSUPA), high-speed packet access (HSPA), long term evolution (LTE), LTE Advanced (LTE-A), 802.11x, Wi-Fi, Zigbee, Ultra-WideBand (UWB), 802.16x, 802.15, home Node-B (HnB), Bluetooth, radio frequency identification (RFID), infrared data association (IrDA), near-field communications (NFC), fifth generation (5G), new radio (NR), or any other wireless or wired device/transceiver for communication.

The communications adapter interconnects the system bus 315 with the cloud environment 129, which may be an outside network, enabling the device 102 to communicate signals (and data) with other such devices (e.g., such as a remote computing system). In one embodiment, the adapter 325 may be connected to one or more I/O buses that are connected to the system bus 315 via an intermediate bus bridge. Suitable I/O buses for connecting peripheral devices such as hard disk controllers, network adapters, and graphics adapters typically include common protocols, such as the Peripheral Component Interconnect (PCI).

The device adapter interconnects input/output devices to the system bus 315, such as a display 341, a control device 342, the camera 104, the lifting tool 105, or the like (e.g., a speaker).

The display 341 is configured to provide one or more UIs or graphic UIs (GUIs) that can be captured by and analyzed by the determination engine 101, as the users interacts with the device 102. Examples of the display 341 can include, but are not limited to, a plasma, a liquid crystal display (LCD), a light emitting diode (LED), a field emission display (FED), an organic light emitting diode (OLED) display, a flexible OLED display, a flexible substrate display, a projection display, a 4K display, a high definition (HD) display, a Retina© display, an in-plane switching (IPS) display or the like. The display 341 may be configured as a touch, three dimensional (3D) touch, multi-input touch, or multi-touch display using resistive, capacitive, surface-acoustic wave (SAW) capacitive, infrared, optical imaging, dispersive signal technology, acoustic pulse recognition, frustrated total internal reflection, or the like as understood by one of ordinary skill in the art for input/output (I/O).

The control device 342, such as a keyboard, a computer mouse, a touchpad, a touch screen, a keypad, or the like, may be further coupled to the system bus 315 for input to the device 102. In addition, one or more inputs may be provided to the computing system 300 remotely via another computing system (e.g., the remote computing system 355) in communication therewith, or the device 102 may operate autonomously.

The camera 104 can be any photosensitive device for capturing one or more images (e.g., still and/or video) of the IOL 110 and the lifting tool 105 with respect to the platform 114 and the cartridge 116. The one or more images can be of any resolution suitable for providing (or determining therefrom) visual information on the locations of the IOL 110 and the lifting tool 105 with respect to the platform 114 and the cartridge 116. Note that the one or more images of the camera 104 can be stored in a common repository, such as the data/web service 140, and can be downloaded (on demand) to and/or from each of the device 102, the device 130, and/or the data/web service 140. The camera 104 can be positioned above the lifting tool 105 to capture a topographical view of the IOL 110. The camera 104 can be stationary (e.g., positioned above the delivery point 115). The camera 104 can move as the lifting tool moves 105. The camera 104 can be representative of multiple cameras, where a first camera is above the pick position 113, a second camera is above the delivery point 115, and/or a third camera moves with the lifting tool 105.

Figure 4:
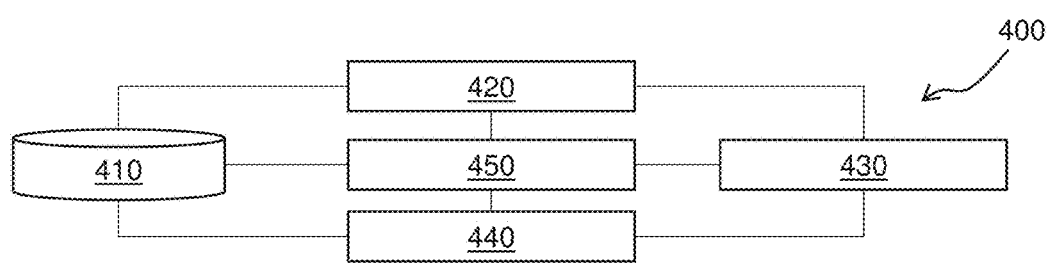
FIG. 4 illustrates an artificial intelligence (AI) diagram of a determination engine according to one or more embodiments.

Generally, the determination engine 101 utilizes the one or more images to guide the automatic placement operations of the lifting tool 105. The determination engine 101 can utilize modules and/or ML/AI algorithms to automatically receive, process, and interpret the one or more images, as well as other data from the common repository. Turning to FIG. 4, an AI diagram 400 of the determination engine 101 is illustrated according to one or more embodiments. The AI diagram 400 includes data 410, a machine 420, a model 430, an outcome 440, and (underlying) hardware 450.

The description of FIG. 4 is made with reference to FIGS. 1-3 for ease of understanding where appropriate. For example, the machine 420, the model 430, and the hardware 450 can represent aspects of the determination engine 101 of FIG. 1 (e.g., a ML/AL algorithm therein), while the hardware 450 can also represent the devices 102 and 130, and/or the data/web service 140 of FIG. 1. In general, the ML/AI algorithms of the AI system 400 (e.g., as implemented by the determination engine 101 of FIG. 1) operate with respect to the hardware 450, using the data 410, to train the machine 420, build the model 430, and predict the outcomes 440.

The data 410 can be any data as described herein. For instance, the data can include IOL information and measurements, such as IOL master data, image data, video data, precision measurement data, three dimensional data, and cartridge data. The data 410 can be on-going data or output data associated with the hardware 450. The data 410 can also include currently collected data, historical data, or other data from the hardware 450. The data 410 can be divided by the machine 420 into one or more subsets.

The machine 420 operates as the controller or data collection associated with the hardware 450 and/or is associated therewith. The machine 420 trains, such as with respect to the hardware 450. This training can also include parsing, analyzing, merging, and correlating of the data 410 collected. In accordance with one or more embodiments, training the machine 420 can include self-training by the determination engine 101 utilizing the one or more subsets.

The model 430 can be an unsupervised learning model, such as a self-discover algorithm, or a supervised learning model, such as a support-vector machine (SVM), that analyze the data 410. For example, a SVM provides a prediction method using a statistical learning framework for classification and regression analysis of the data 410. The model 430 can employ any combination of classification, clustering, regression, anomaly detection, data cleaning, reinforcement learning, structured prediction, feature engineering or learning, semi-supervised learning, decision trees, linear regression, neural or artificial neural networks, logistic regression, recursive selection, relevance vector, and support vector operations, or the like.

The model 430 (e.g., a ML/AI model and/or resulting determination model) is built on the data 410 associated with the hardware 450. Building the model 430 can include physical hardware or software modeling, algorithmic modeling, and/or the like that seeks to represent the data 410 (or subsets thereof) that has been collected and trained. In some aspects, building of the model 430 is part of self-training operations by the machine 420.

The model 430 can be configured to model the operation of hardware 450 and model the data 410 collected from the hardware 450 to predict the outcome 440 (e.g., achieve automatic placement of the IOL 110 at a target orientation on/in the cartridge 116 or on the features 117 of the cartridge 116) achieved by the hardware 450. Predicting the outcomes 440 (of the model 430 associated with the hardware 450) can utilize a trained model 430. Thus, using the outcome 440 that is predicted, the machine 420, the model 430, and the hardware 450 can be further configured and/or refined, accordingly.

Thus, for the AI diagram 400 to operate with respect to the hardware 450, using the data 410, to train the machine 420, build the model 430, and predict the outcomes 440, the ML/AI algorithms therein can include neural networks. In general, a neural network is a network or circuit of neurons, or in a modern sense, an artificial neural network (ANN), composed of artificial neurons or nodes or cells. For example, an ANN involves a network of processing elements (artificial neurons) which can exhibit complex global behavior, determined by the connections between the processing elements and element parameters. These connections of the network or circuit of neurons are modeled as weights. A positive weight reflects an excitatory connection, while negative values mean inhibitory connections. Inputs are modified by a weight and summed using a linear combination. An activation function may control the amplitude of the output. For example, an acceptable range of output is usually between 0 and 1, or it could be −1 and 1. In most cases, the ANN is an adaptive system that changes its structure based on external or internal information that flows through the network.

In more practical terms, neural networks are non-linear statistical data modeling or decision-making tools that can be used to model complex relationships between inputs and outputs or to find patterns in data. Thus, ANNs may be used for predictive modeling and adaptive control applications, while being trained via a dataset. Note that self-learning resulting from experience can occur within ANNs, which can derive conclusions from a complex and seemingly unrelated set of information. The utility of artificial neural network models lies in the fact that they can be used to infer a function from observations and also to use it. According to one or more embodiments, the neural network can implement a long short-term memory neural network architecture, a convolutional neural network (CNN) architecture, or other the like. The neural network can be configurable with respect to a number of layers, a number of connections (e.g., encoder/decoder connections), a regularization technique (e.g., dropout); and an optimization feature.

Figure 5:
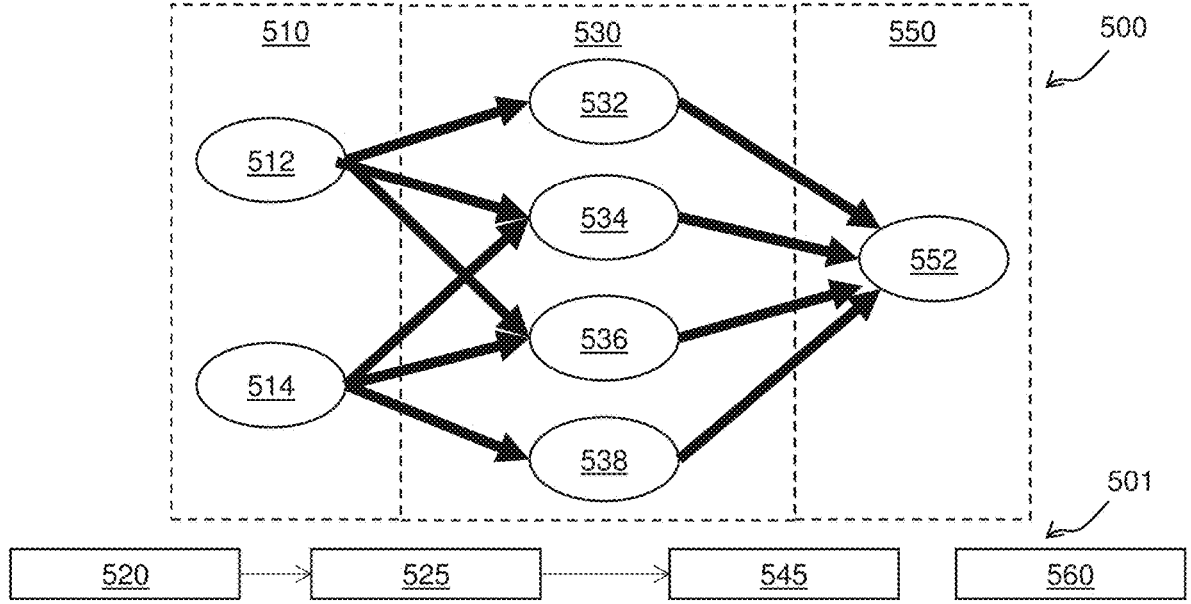
FIG. 5 illustrates a neural network and a method performed in the neural network according to one or more embodiments.

Turning now to FIG. 5, a neural network 500 and a method 501 performed in the neural network 500 are shown according to one or more embodiments. The neural network 500 operates to support implementation of the ML/AI algorithms (e.g., as implemented by the determination 101 of FIG. 1) described herein. The neural network 500 can be implemented in hardware, such as the machine 420 and/or the hardware 450 of FIG. 4. As indicated herein, the description of FIG. 5 is made with reference to FIGS. 1-4 for ease of understanding where appropriate.

In an example operation, the determination 101 of FIG. 1 includes collecting the data 410 from the hardware 450. In the neural network 500, an input layer 510 is represented by a plurality of inputs (e.g., inputs 512 and 514 of FIG. 5). With respect to block 520 of the method 501, the input layer 510 receives the inputs 512 and 514.

At block 525 of the method 501, the neural network 500 encodes the inputs 512 and 514 utilizing any portion of the data 410 (e.g., the dataset and predictions produced by the AI system 400) to produce a latent representation or data coding. The latent representation includes one or more intermediary data representations derived from the plurality of inputs. According to one or more embodiments, the latent representation is generated by an element-wise activation function (e.g., a sigmoid function or a rectified linear unit) of the determination engine 101 of FIG. 2. As shown in FIG. 5, the inputs 512 and 514 are provided to a hidden layer 530 depicted as including nodes 532, 534, 536, and 538. The neural network 500 performs the processing via the hidden layer 530 of the nodes 532, 534, 536, and 538 to exhibit complex global behavior, determined by the connections between the processing elements and element parameters. Thus, the transition between layers 510 and 530 can be considered an encoder stage that takes the inputs 512 and 514 and transfers it to a deep neural network (within the layer 530) to learn some smaller representation of the input (e.g., a resulting the latent representation).

The deep neural network can be a CNN, a long short-term memory neural network, a fully connected neural network, or combination thereof. This encoding provides a dimensionality reduction of the inputs 512 and 514. Dimensionality reduction is a process of reducing the number of random variables (of the inputs 512 and 514) under consideration by obtaining a set of principal variables. For instance, dimensionality reduction can be a feature extraction that transforms data (e.g., the inputs 512 and 514) from a high-dimensional space (e.g., more than 10 dimensions) to a lower-dimensional space (e.g., 2-3 dimensions). The technical effects and benefits of dimensionality reduction include reducing time and storage space requirements for the data 410, improving visualization of the data 410, and improving parameter interpretation for ML. This data transformation can be linear or nonlinear. The operations of receiving (block 520) and encoding (block 525) can be considered a data preparation portion of the multi-step data manipulation by the determination engine 101.

At block 545 of the method 510, the neural network 500 decodes the latent representation. The decoding stage takes the encoder output (e.g., the resulting the latent representation) and attempts to reconstruct some form of the inputs 512 and 514 using another deep neural network. In this regard, the nodes 532, 534, 536, and 538 are combined to produce in the output layer 550 an output 552, as shown in block 560 of the method 510. That is, the output layer 550 reconstructs the inputs 512 and 514 on a reduced dimension but without the signal interferences, signal artifacts, and signal noise.

Figure 7:
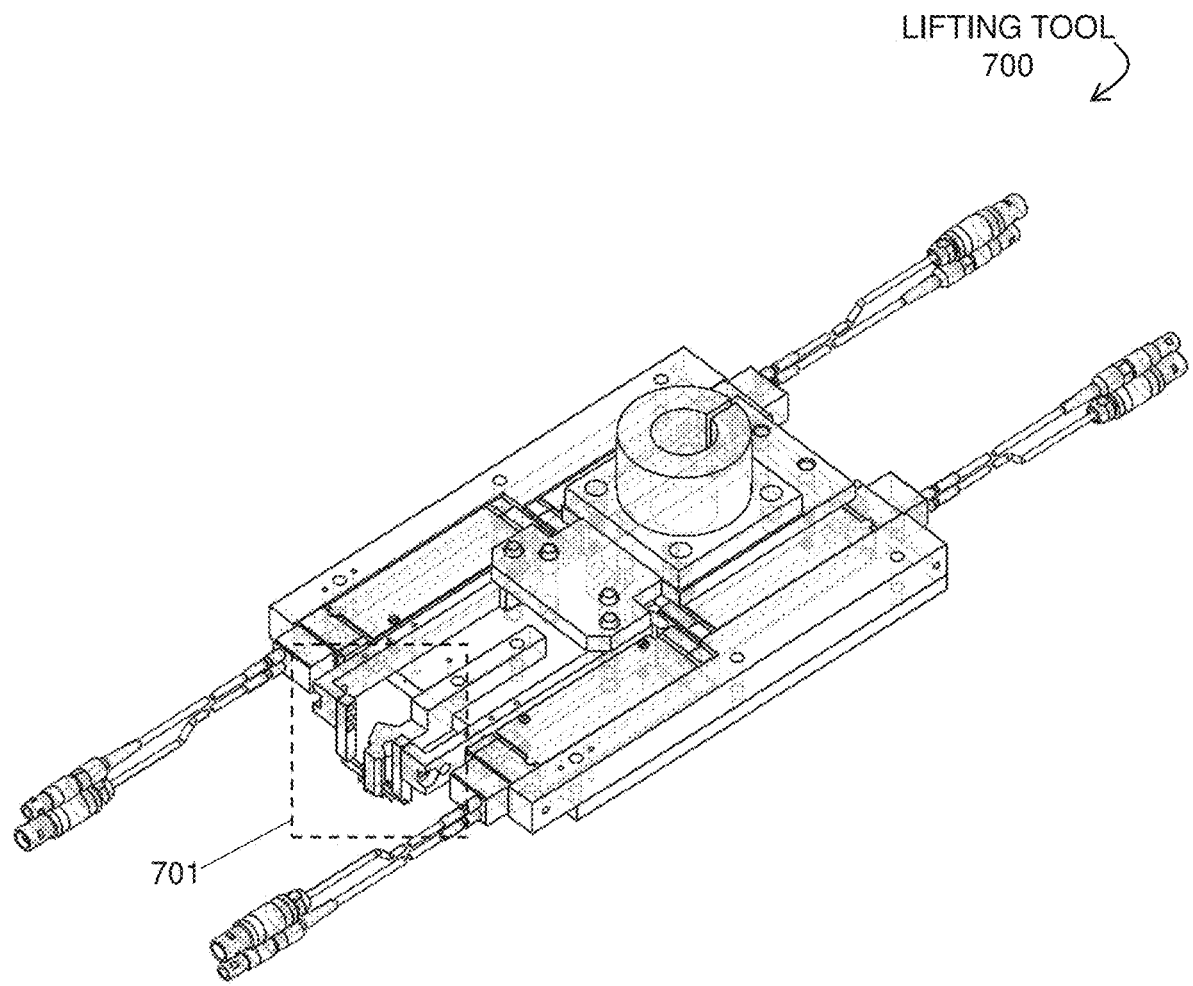
FIG. 7 illustrates a lifting tool according to one or more embodiments.
Figure 8A:
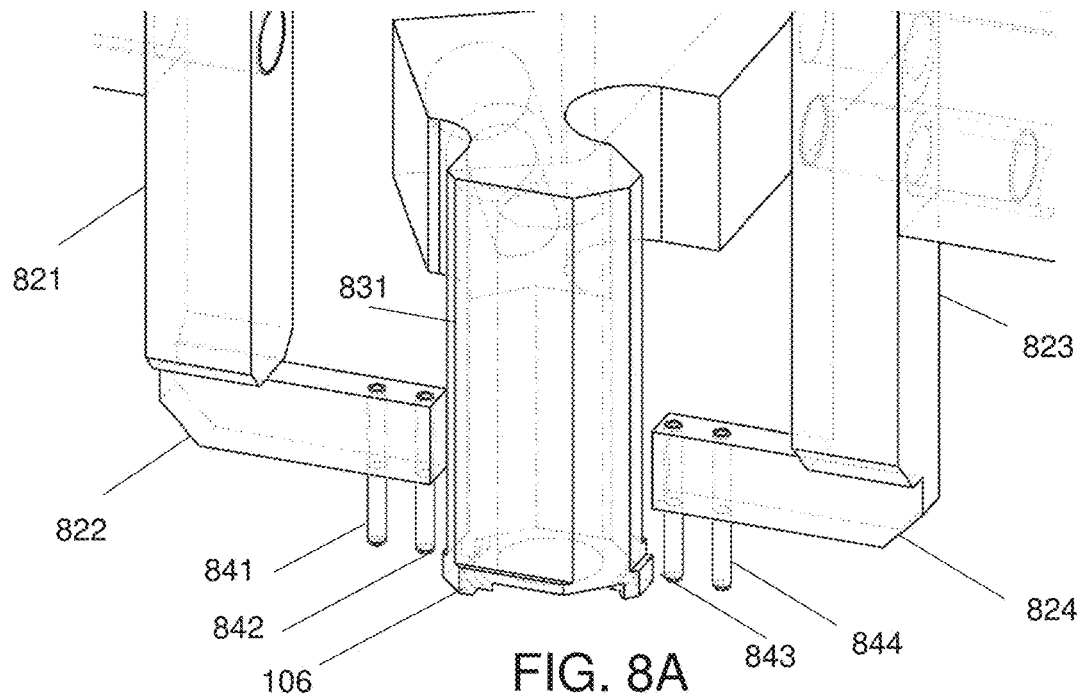
FIGS. 8A and 8B show perspective views of a portion of the lifting tool of FIG. 7 according to one or more embodiments.
Figure 8B:
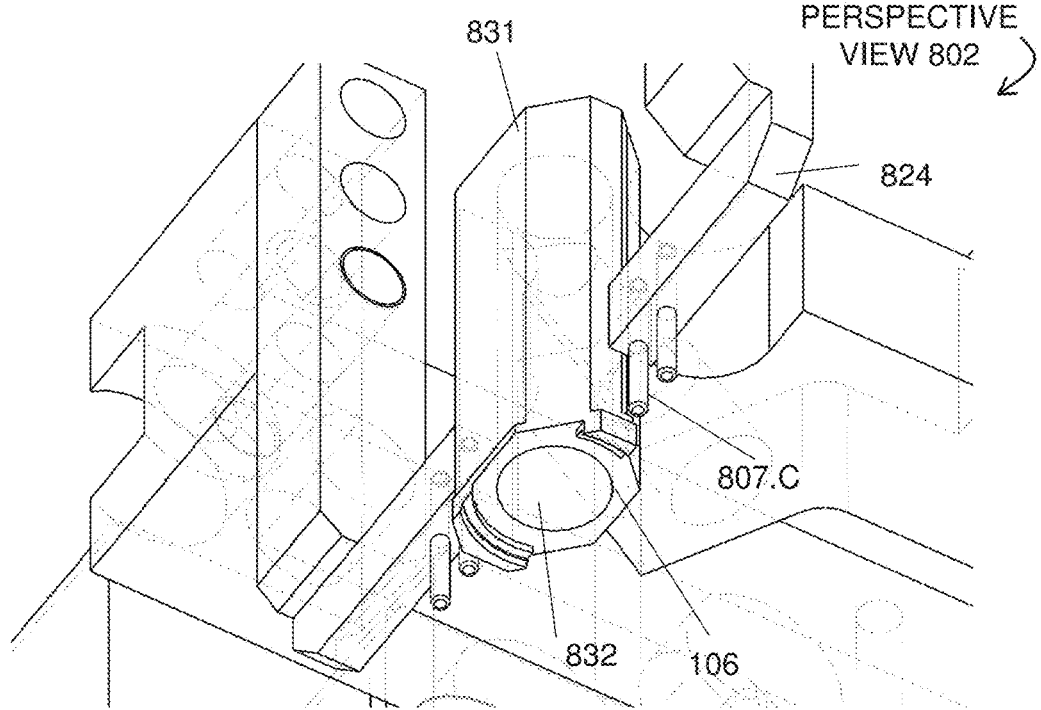
Figure 9A:
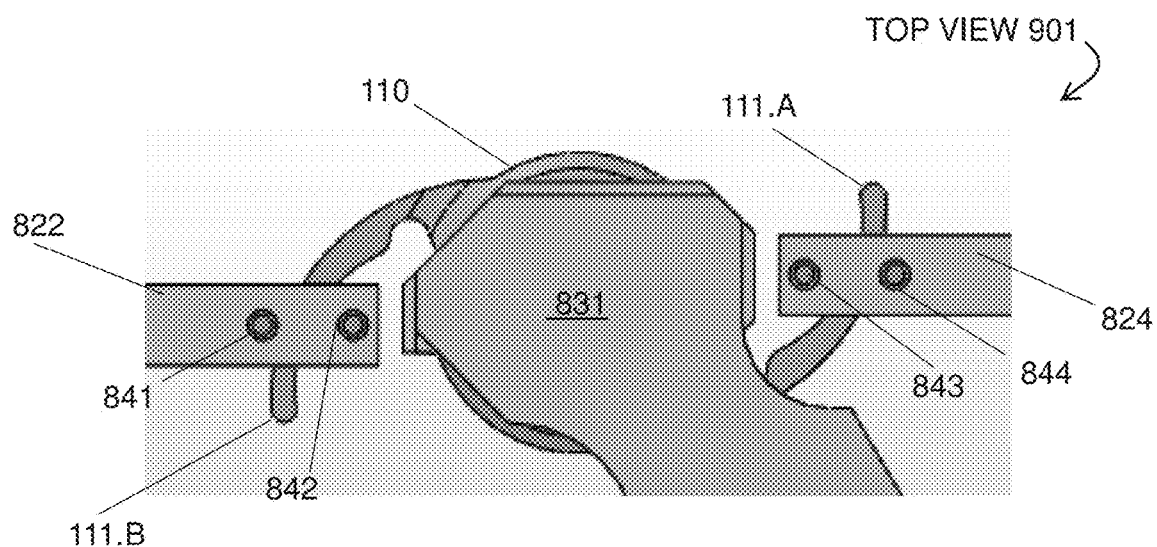
FIGS. 9A and 9B show top and bottom views of an IOL in contact with a lifting tool according to one or more embodiments.
Figure 9B:
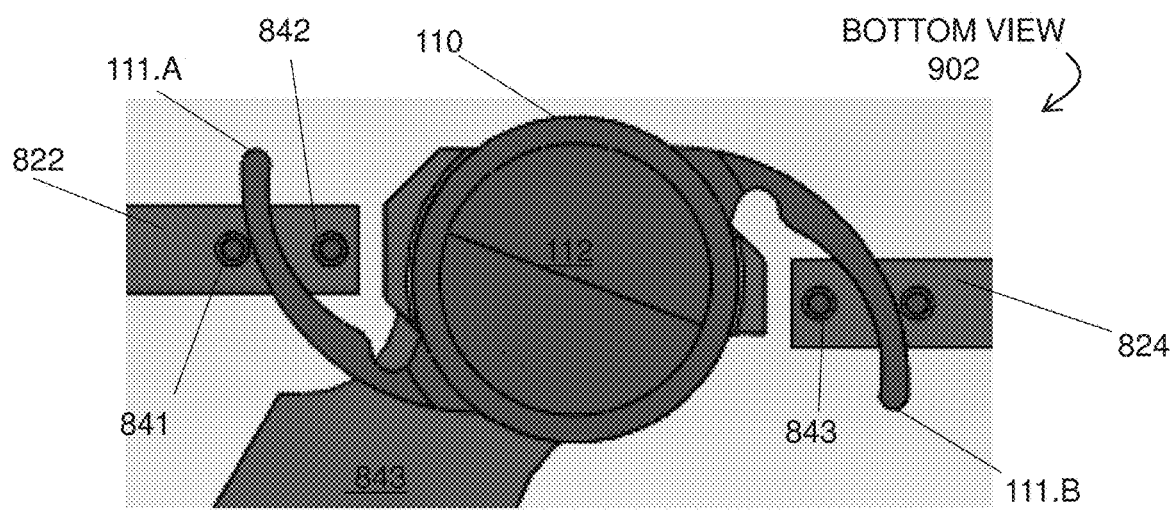
Figure 10:
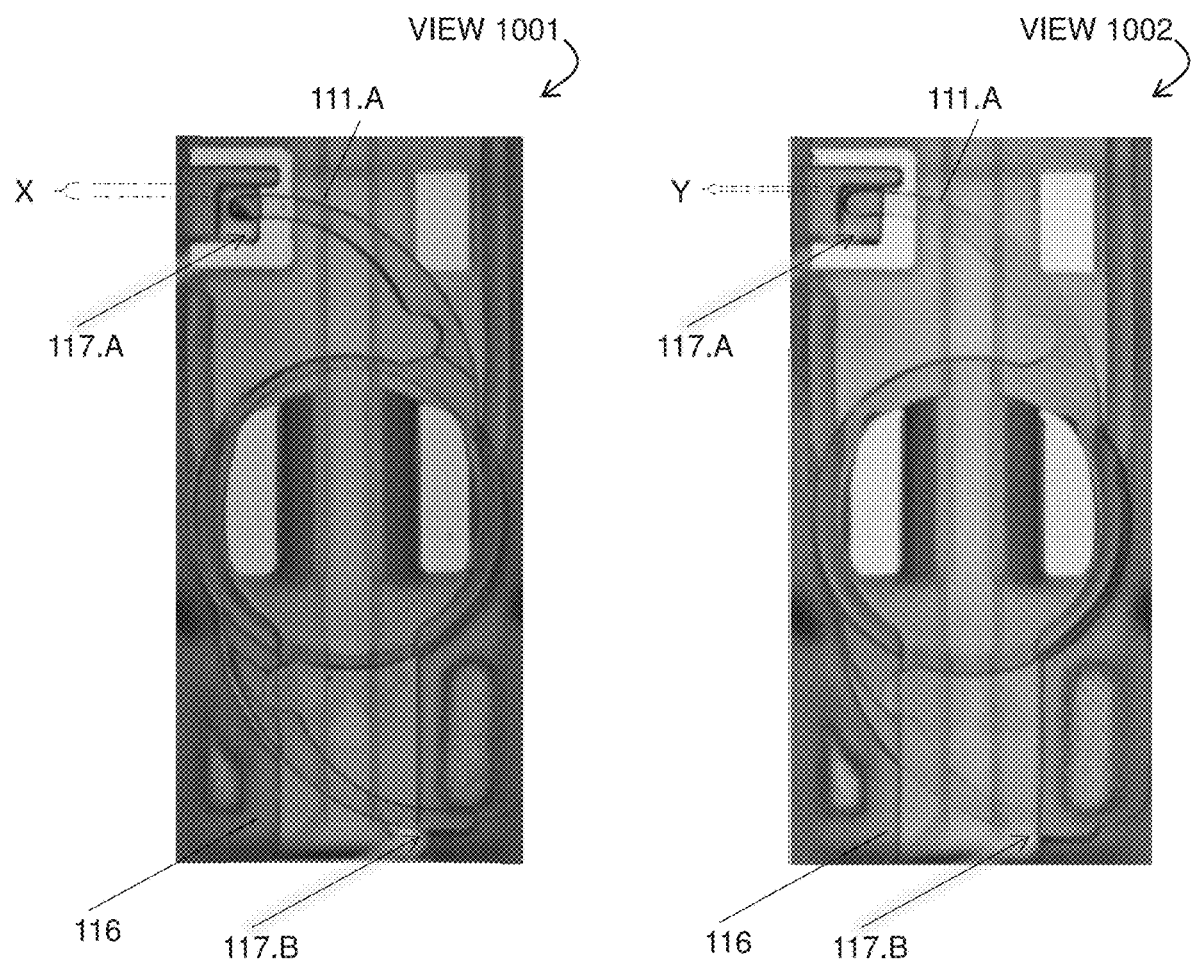
FIG. 10 show images detailing position changes of an IOL based on operations of a system according to one or more embodiments.

Turning to FIG. 6, a method 600 is illustrated according to one or more embodiments. The method 600 depicts a general automatic placement operation of the IOL 110 in the cartridge 116 of the system 100. In supplement to FIG. 6, FIGS. 7-10 are provided. FIG. 7 illustrates a lifting tool 700 according to one or more embodiments. The lifting tool 700 is a schematic example of the lifting tool 105 of the system 100. FIGS. 8A and 8B show perspective views 801 and 802 of a portion 701 of the lifting tool 700 of FIG. 7 according to one or more embodiments. As shown in FIGS. 7, 8A, and 8B, the lifting tool 700 includes frame members 821, 822, 823, and 824, a central member 831, which includes a bore 832, and grippers 841, 842, 843, and 844. FIGS. 9A and 9B show top and bottom views 901 and 902 of the IOL 110 in contact with the lifting tool 700 of FIG. 7 according to one or more embodiments. FIG. 10 show images 1001 and 1002 detailing position changes of the IOL 110 based on operations of the lifting tool 700 of FIG. 7 according to one or more embodiments. For brevity, like reference numerals in the figures indicate like elements, and objects, elements, items, and reference numerals that are similar to those of previous figures are reused for FIGS. 6-10.

The method 600 begins at block 605, when the camera 104 captures one or more images of the lifting tool 700, the IOL 110, and the haptics 111 with respect to the platform 114. Note that the camera 104 can capture the one or more images intermittently or continuously, such that visual information is fed throughout the method 600 to the device 102. Oval A illustrates a non-limiting example of how the camera 104 can capture the one or more images and provide the visual information at a later time in the method 600 (e.g., the camera 104 captures one or more images of the IOL 110 and the haptics 111 with respect to the cartridge 116). Thus, the system 100 provides a guided vision for automatic placement.

At block 610 (e.g., see block 210 of FIG. 2), the nozzle head 108 of the lifting tool 105 seizes the IOL 110 from the pick position 113 of the platform 114 based on the airflow 109 through the nozzle head 108. Utilizing sensors of the lifting tool 105, the determination engine 101 can regulate the airflow 109 so as not to bend or damage the IOL 110. Note that the determination engine 101 utilizes the visual information to confirm the lifting tool 105 is in position above the pick position 113. Turning to FIGS. 9A and 9B, the top and bottom views 901 and 902 of the IOL 101 seized by the central member 831. Note that the first haptic 111.A is between the grippers 841 and 842 and that the second haptic 111.B is between the grippers 843 and 844.

At block 630 (e.g., see block 210 of FIG. 2), the lifting tool 105 deposits the IOL 110 at the delivery point 115 in the cartridge 116 by changing (e.g., reducing or stopping) the airflow 109 through the nozzle head 108. Note that the determination engine 101 utilizes the visual information to confirm the lifting tool 105 is in position above the delivery point 115. Turning to FIG. 10, image 1001 provides visual information of the IOL 110 within the cartridge 116.

At block 650, the determination engine 101 determines a location of at least one of the one or more haptics 111 of the IOL 110 with respect to a matching one of the one or more features 117 of the cartridge 116 (e.g., a first haptic 111.A is determined with respect to a first feature 117.A). Generally, the determination engine 101 determines incremental positional statuses of the IOL 110 and the haptics 111 with respect to the pick position 113, the delivery point 115, and the features 117 throughout the method 600. Returning to FIG. 10, note that, in the image 1001, the first haptic 111.A is separated from a wall of the first feature 117.A by a distance X. The distance X is determined by the determination engine 101. According to one or more embodiments, the features 117.A and 117.B of FIG. 10 include a flat seat or table top like surface with at least one wall extending perpendicular from an edge of that surface.

At decision block 655, the determination engine 101 determines whether a target location is achieved. The target location can be when the haptic 111 is adjacent, next to, or otherwise in contact with the wall of the feature 117. For instance, the determination engine 101 determines whether the distance X at a value where the IOL 110 is properly loaded into the cartridge 116 and can be properly folded without being damaged. If the target location is achieved (e.g., an alignment), the method 600 proceeds (e.g., as shown by the YES arrow) to block 680. If the target location is not achieved (e.g., a misalignment), the method 600 proceeds (e.g., as shown by the NO arrow) to block 270.

At block 670 (e.g., see block 270 of FIG. 2), when there is a misalignment, the determination engine 101 causes the lifting tool 105 to adjust at least one of the haptics 111 from a current location to the target location. Sub-block 672 further describes the operation of block 670. At sub-block 672, one or more frame members 821, 822, 823, and 824 and/or one or more grippers 841, 842, 843, and 844 can be actuated to adjust the haptics 111 from the current location to a subsequent orientation (i.e., the end goal of achieving the target location). For instance, the grippers 841 and 842 can move laterally with the frame member 822 so as to contact the first haptic 111.A and adjust its position. Note that, according to one or more embodiments, the grippers 841, 842, 843, and 844 can be independently movable from the nozzle head 106 and the one or more frame members 821, 822, 823, and 824. The method 600, then, loops through block 650 and decision block 655 to determine if further adjustment is required. For instance, the determination engine 101 determines whether a distance Y of image 1002 is at a value where the IOL 110 is properly loaded into the cartridge 116 and can be properly folded without being damaged. Since the distance Y is acceptable (at or near zero), the process proceeds to block 680.

At block 680, the determination engine 101 determines a location of at least one of the one or more haptics 111 of the IOL 110 with respect to a matching one of the one or more features 117 of the cartridge 116 (e.g., a second haptic 111.B is determined with respect to a second feature 117.B). Note that the visual information generated by the camera 104 at block 610 can be continually fed to the determination engine 101, as demarcated by the oval A.

At decision block 685, determination engine 101 determines whether the target location is achieved. If the target location is achieved (e.g., an alignment), the method 600 proceeds (e.g., as shown by the YES arrow) to block 690 and ends. If the target location is not achieved (e.g., a misalignment), the method 600 proceeds (e.g., as shown by the NO arrow) to block 695.

At block 695, when there is a misalignment, the determination engine 101 causes the lifting tool 105 to adjust at least one of the haptics 111 from a current location to the target location. Sub-block 672 further describes the operation of block 670. By way of example, the determination engine 101 causes the lifting tool 700 to adjust the second haptic 111.B from the second location to a target location on the second feature 117.B of the cartridge 116. The method 600, then, loops through block 680 and decision block 685 to determine if further adjustment is required. If the IOL 110 is properly loaded, the method 600 proceeds to block 690.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Although features and elements are described above in particular combinations, one of ordinary skill in the art will appreciate that each feature or element can be used alone or in any combination with the other features and elements. In addition, the methods described herein may be implemented in a computer program, software, or firmware incorporated in a computer-readable medium for execution by a computer or processor. A computer readable medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Examples of computer-readable media include electrical signals (transmitted over wired or wireless connections) and computer-readable storage media. Examples of computer-readable storage media include, but are not limited to, a register, cache memory, semiconductor memory devices, magnetic media such as internal hard disks and removable disks, magneto-optical media, optical media such as compact disks (CD) and digital versatile disks (DVDs), a random access memory (RAM), a read-only memory (ROM), an erasable programmable read-only memory (EPROM or Flash memory), a static random access memory (SRAM), and a memory stick. A processor in association with software may be used to implement a radio frequency transceiver for use in a terminal, base station, or any host computer.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The descriptions of the various embodiments herein have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for automatic placement of a lens in a cartridge, the method comprising:
    seizing, by a nozzle head of a lifting tool, the lens from a pick position of a platform based on an air flow through the nozzle head;
    depositing, by the lifting tool, the lens at a delivery point in the cartridge by changing the air flow through the nozzle head;
    determining, by at least one processor coupled to the lifting tool, a location of a haptic of the lens with respect to a feature of the cartridge; and
    adjusting, by the lifting tool, the haptic from the location to a target orientation on the cartridge when the location of the haptic is determined to be misaligned with the feature.

2. The method of claim 1, further comprising:
    determining, by the at least one processor from one or more images, incremental positional statuses of the lens and the haptic of the lens with respect to the pick position, the delivery point, and the feature.

3. The method of claim 1, further comprising:
    capturing, by a camera coupled to the at least one processor, one or more images of the lens and the haptic of the lens with respect to the platform and the cartridge to provide a guided vision to the at least one processor.

4. The method of claim 1, wherein the lifting tool contacts only non-optical portions of the lens during the seizing of the lens.

5. The method of claim 1, further comprising:
    actuating a gripper of the lifting tool to adjust the haptic from the location to the target orientation based on signals from the at least one processor from one or more images.

6. The method of claim 1, further comprising:
    determining, by the at least one processor, a second location of a second haptic of the lens with respect to a second feature of the cartridge; and
    adjusting, by the lifting tool, the second haptic from the second location to a target orientation on the cartridge when the second location of the haptic is determined to be misaligned with the second feature.

7. The method of claim 1, wherein the lifting tool comprises first and second grippers, each configured to adjust one of the haptics of the lens.

8. The method of claim 1, wherein the nozzle head contacts an outer periphery of a body the lens.

9. The method of claim 1, wherein the feature of the cartridge comprises a flat surface with at least one wall extending perpendicular from an edge of that surface.

10. The method of claim 1, wherein the lifting tool comprises a frame, one or more grippers, and the nozzle head, the frame comprising one or more members, each of which is configured to articulate and move with respect to x-y-z directions.

11. A system for automatic placement of a lens in a cartridge, the system comprising:
    a lifting tool comprising a nozzle head, the lifting tool being configured to:
        seize the lens from a pick position of a platform based on an air flow through the nozzle head,
        deposit the lens at a delivery point in the cartridge by changing the air flow through the nozzle head, and
        adjust a haptic of the lens from a location of the haptic to a target orientation on the cartridge when the location of the haptic is determined to be misaligned with a feature of the cartridge, and
    at least one processor coupled to the lifting tool, the at least one processor being configured to determine the location of the haptic with respect to the feature of the cartridge.

12. The system of claim 11, wherein the at least one processor is configured to determine, from one or more images, incremental positional statuses of the lens and the haptic of the lens with respect to the pick position, the delivery point, and the feature.

13. The system of claim 11, wherein the system comprises a camera coupled to the at least one processor, the camera configured to capture one or more images of the lens and the haptic of the lens with respect to the platform and the cartridge to provide a guided vision to the at least one processor.

14. The system of claim 11, wherein the lifting tool contacts only non-optical portions of the lens during the seizing of the lens.

15. The system of claim 11, wherein the system comprises a gripper actuated by the lifting tool and configured to adjust the haptic from the location to the target orientation based on signals from the at least one processor from one or more images.

16. The system of claim 11, wherein the at least one processor is configured to determine a second location of a second haptic of the lens with respect to a second feature of the cartridge, and
    wherein the lifting tool is configured to adjust the second haptic from the second location to a target orientation on the cartridge when the second location of the haptic is determined to be misaligned with the second feature.

17. The system of claim 11, wherein the lifting tool comprises first and second grippers, each configured to adjust one of the haptics of the lens.

18. The system of claim 11, wherein the nozzle head contacts an outer periphery of a body the lens.

19. The system of claim 11, wherein the feature of the cartridge comprises a flat surface with at least one wall extending perpendicular from an edge of that surface.

20. The system of claim 11, wherein the lifting tool comprises a frame, one or more grippers, and the nozzle head, the frame comprising one or more members, each of which is configured to articulate and move with respect to x-y-z directions.

* * * * *